# (12) United States Patent
Szeles

(10) Patent No.: US 7,336,993 B1
(45) Date of Patent: Feb. 26, 2008

(54) THERAPY APPLIANCE FOR PUNCTUAL STIMULATION

(76) Inventor: Josef Constantin Szeles, Glanzinggasse 5/7, A-1190 Wien (AT)

( * ) Notice: Subject to any disclaimer, the term of this patent is extended or adjusted under 35 U.S.C. 154(b) by 463 days.

(21) Appl. No.: 10/129,919

(22) PCT Filed: Nov. 13, 2000

(86) PCT No.: PCT/AT00/00297

§ 371 (c)(1),
(2), (4) Date: Aug. 23, 2002

(87) PCT Pub. No.: WO01/35897

PCT Pub. Date: May 25, 2001

(30) Foreign Application Priority Data

Nov. 12, 1999 (AT) .................................. 786/99 U

(51) Int. Cl.
*A61N 1/04* (2006.01)

(52) U.S. Cl. .......................................... 607/2; 128/907
(58) Field of Classification Search ................ 128/907; 600/554, 557; 607/2, 45–46, 50
See application file for complete search history.

(56) References Cited

U.S. PATENT DOCUMENTS

| 5,012,816 A | | 5/1991 | Lederer | |
|---|---|---|---|---|
| 5,058,605 A | * | 10/1991 | Slovak | 607/72 |
| 5,449,378 A | * | 9/1995 | Schouenborg | 607/46 |
| 5,578,065 A | * | 11/1996 | Hattori et al. | 607/46 |
| 5,957,951 A | | 9/1999 | Cazaux et al. | |
| 6,445,955 B1 | * | 9/2002 | Michelson et al. | 607/46 |

FOREIGN PATENT DOCUMENTS

| DE | 297 20 785 | 2/1998 |
|---|---|---|
| JP | 04 314459 | 3/1993 |

* cited by examiner

*Primary Examiner*—Kristen D. Mullen
(74) *Attorney, Agent, or Firm*—Collard & Roe, P.C.

(57) ABSTRACT

A punctual stimulation therapy appliance (1) comprising a battery-operated treatment current generator (2) which is arranged in a small housing (5) to be worn on the body in the region of the outer ear and which feeds a punctual stimulation electrode (4) connected thereto via at least one flexible line (3). The treatment current generator (2) is provided with a programmable microchip (17) controlling the treatment current course which microchip preferably is a microprocessor, or a microcontroller, respectively. Preferably, the housing (5) of the appliance (1) approximately has the shape of a calotte and carries a surface electrode disk (7) designed to be adhesive.

13 Claims, 1 Drawing Sheet

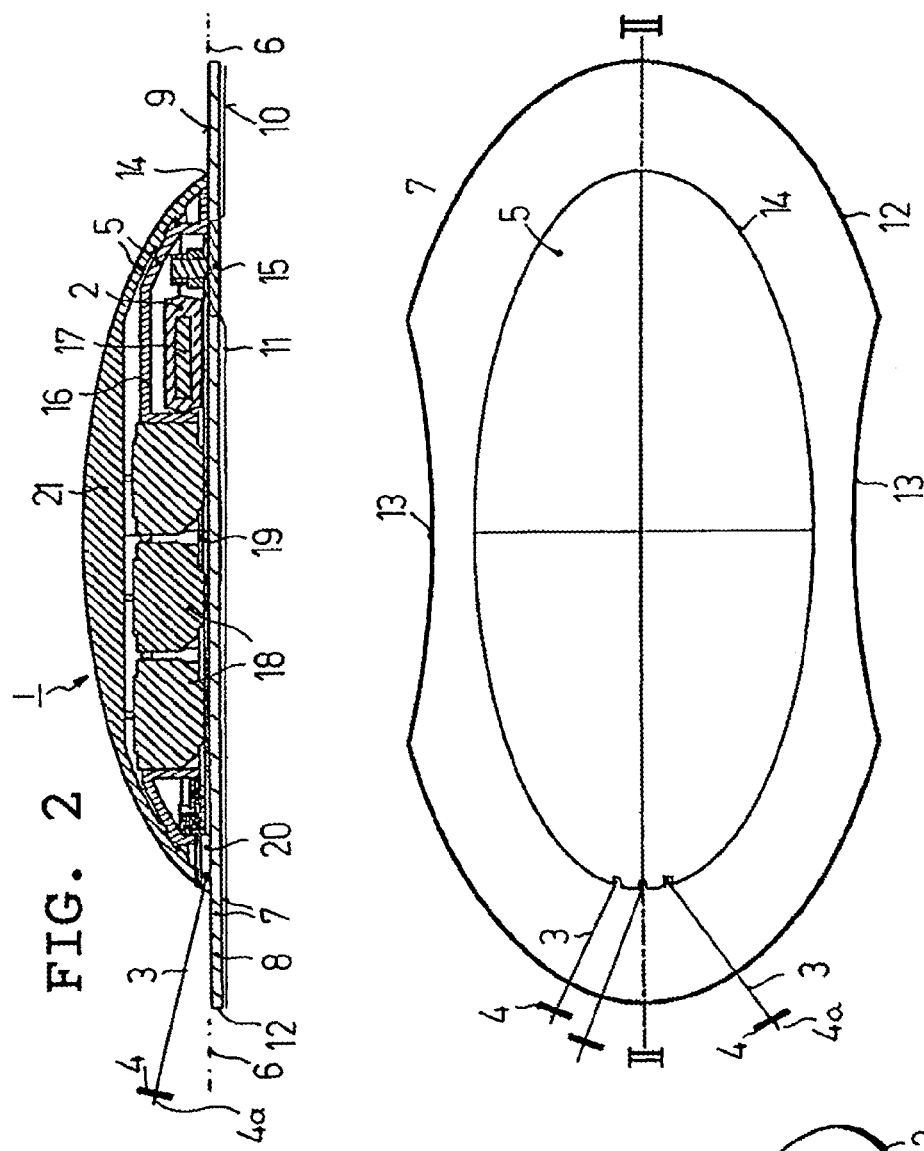
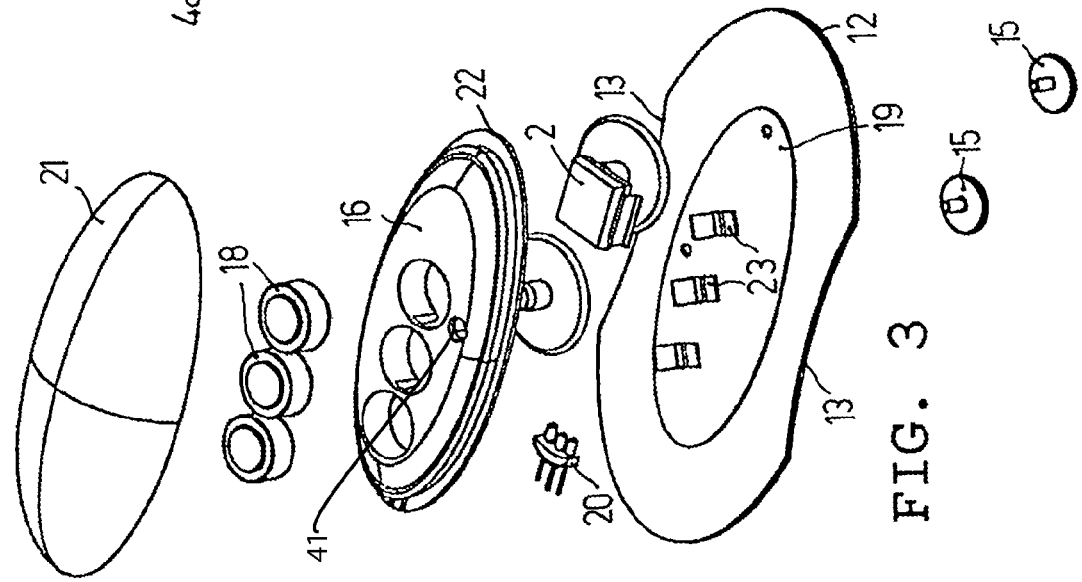

THERAPY APPLIANCE FOR PUNCTUAL STIMULATION

The invention relates to a punctual stimulation therapy appliance comprising a portable battery-operated treatment current generator, said generator feeding at least one electrode connected via a flexible line, which electrode is to be arranged at a receptor region located under the surface of the skin.

The electric punctual stimulation therapy which also includes various forms of electro-acupuncture may be successfully employed in various health disturbances, such as, e.g., allergies, asthma, adipositas, pain. In an electric punctual stimulation therapy, often a treatment which lasts for several hours or even several days is considered to be favorable. In this respect, the mobility of the patients to be treated is to be restricted as little as possible, and, as far as possible, the treatment should be feasible within the scope of a largely normal way of life, including working on a paid job. Thus, it is an object forming the basis of the present invention to provide a therapy appliance which has a simple construction and is easy to produce, which can be positioned on the body, in the region of the ear, in a simple manner without unpleasant appearance, and which will find a good support there without any additional measures and can be worn over extended periods of time, with the appliance possibly not having any detrimental mechanical effect on the electrode supply lines and on the seat of the electrode during such treatment. Taking into consideration the above-mentioned factors, or characteristics, respectively, to be attained, the appliance to be provided shall make it possible to select and adjust, respectively, from among a great many variants that course of treatment current which is favorable for its respective application, wherein it shall be possible to choose between various curve forms, pulse forms and frequencies of the treatment current, from various time-dependent variations of the intensity of the treatment current, and also among various possible durations of current flow intervals and current flow pauses within the course of treatment sequences and also with a view to the duration of pauses of rest between treatment sequences.

By this design, the object set out above can well be met in a simple manner and with low expenditures. By designing the treatment current generator with a microchip capable of being programmed, it becomes possible to choose, in a simple manner, a course of treatment current optimally corresponding to each individual case treated without having to employ a larger number of further circuit elements therefor, so that the treatment current generator can be made with very small dimensions, allowing for a correspondingly small and light-weight design of the appliance which thereby can be placed on the body in the region of the ear, without any problems in a manner ensuring a good, stable fit of the appliance over extended periods of time, and thereby keeping low the risk of undesired mechanical influences on the connecting lines leading to the punctual stimulation electrodes, and thus, furthermore, to these electrodes themselves.

It is possible to produce a treatment current generator with a very small construction which can be realized at low costs, which treatment current generator will not require any repeated operation by the patient to be treated even in case of long lasting treatments using different treatment current courses, so that no adjustment manipulations possibly adversely affecting its fit have to be carried out on the appliance, and by controlling the treatment current course by means of the microchip capable of being programmed, a plurality of variants of the treatment current course can be provided by simple programming of the chip. Not only is it possible to provide manifold pattern forms of the treatment current in terms of waveform and amplitude, but also a plurality of treatment current patterns in terms of short-time current interruptions in individual treatment sequences and in terms of extended pauses between treatment sequences can be provided. An embodiment extensively utilizing these manifold possibilities is characterized in that the programmable microchip may be programmed from the outside each for the digital synthesis of the respective desired waveform and amplitude of the treatment current. Another embodiment which is characterized in that the programmable microchip is provided with a memory in which several waveforms and amplitudes of the treatment current are stored and selectively can be called makes it possible for a therapist to simply select from a group of treatment current patterns a treatment current course that seems particularly suitable for the specific case and, optionally in the course of a longer treatment series, influences the treatment course by changing the selection. Correspondingly, it may also be provided that the programmable microchip is provided with a memory in which in each case several values for the duration of current flow intervals and current flow pause intervals to be used in treatment sequences and/or for the duration of rest pauses to be provided between treatment sequences can be stored and optionally called. In this case, again, a simple selection from several possibilities is feasible. A larger spectrum of possibilities regarding the realization of certain pauses in the course of treatment sequences and longer resting times between consecutive treatment sequences are provided by an embodiment which is characterized in that the programmable microchip may be programmed for controlling the length of the current flow intervals and current flow pause intervals in the course of treatment sequences and/or the duration of rest pauses provided between the treatment sequences.

According to a preferred embodiment of the inventive punctual stimulation therapy appliance, the programmable microchip is a microprocessor, or micro-controller, respectively. This results in advantages in terms of effecting a programming and in terms of attaining a greater variety of variants of the treatment current course; furthermore, this embodiment can simply be realized at relatively low expenditures.

For a stable, good fit of the appliance according to the invention over extended periods of time at a site of the skin surface and also for meeting the object that the appliance should not be very disturbing to its carrier also over extended periods of time, an embodiment of this appliance is advantageous which is characterized in that the housing of the appliance approximately has the geometrical form of a calotte cut from an ellipsoid, and, at the base of the calotte carries a flexible surface (area) electrode disk laterally projecting beyond the base and designed to be adhesive at its side facing away from the calotte, which surface electrode disk is provided as a base electrode for supplying the treatment current and connected to the treatment current generator. By this calotte shape not only a mostly desired inconspicuous appearance is obtained, but also the influence of mechanical forces which might adversely affect the fit of the appliance is reduced, and, moreover, the stability of the fit of the appliance is particularly aided by the laterally projecting surface electrode disk designed to be adhesive. By this lateral projection of this disk, the rim thereof may be snugly pressed to the respective location on the body in a simple manner, and the disk can cling to the body site without any problems, whereby a particularly good fit will be obtained.

As regards the design of the surface electrode disk, it is advantageous for structural reasons and also for the desired snug fitting property if it is provided for the surface electrode disk to be a disk formed of electrically insulating flexible material which with its one surface side is seated on the housing of the appliance and at its other surface side which faces away from the housing of the appliance has an electrically conductive layer. For construction purposes it is suitable if the electrically conductive layer of the surface electrode disk is connected to the treatment current generator by contact connectors passing through the insulating material of the disk. Furthermore, it is advantageous for a good electrical and mechanical contact if an electrically conductive gel is provided for intensifying the electrical and mechanical contact between the side of the surface electrode disk provided with the electrically conductive layer and the surface of the skin.

For positioning the appliance behind the ear, it is suitable if it is provided for the surface electrode disk on at least one site of its peripheral rim to have an indentation and otherwise to project substantially all around to an equal width beyond the rim of the base of the calotte.

A particularly structurally suitable embodiment of the appliance according to the invention is characterized in that the housing of the appliance has an inner housing part accommodating the treatment current generator provided with the programmable microchip, feeding batteries, a printed board forming electrical connections, and treatment current output contacts, and an outer housing part having the shape of a calotte-type cap capable of being snapped on the inner housing part so as to cover the latter, the surface electrode disk being fixed at the rim of the inner housing part.

From the functional viewpoint it often is suitable, particularly if the appliance designed according to the invention is intended for a single use only, if it is provided for a switch to be arranged in the inner housing part, which switch is included in the current supply of the treatment current generator and which, in the at-rest position, is in its "OFF" position and can be moved into its "ON" position by pressing thereon, a pin for pressing thereon being provided on the outer housing part, the switch being movable into its "ON" position by means of this pin when the outer housing part is snapped onto the inner housing part.

The invention will now be explained in more detail by way of examples and with reference to the schematic drawings.

In the drawings,

FIG. 1 shows an embodiment of the punctual stimulation therapy appliance designed according to the invention in top view, FIG. 2 shows this appliance in a section according to line II-II of FIG. 1, and FIG. 3 shows essential parts of this appliance in exploded view.

The embodiment of the punctual stimulation therapy appliance 1 designed according to the invention and illustrated in the drawings may, e.g., have a size of a quarter of the illustrations of FIGS. 1 and 2. The appliance 1 is provided with a battery-operated treatment current generator 2 which feeds electrodes 4 connected via flexible lines 3. In the instance illustrated, such electrodes 4 which are provided for stimulating receptor regions which are located at various sites below the surface of the skin have needle points 4a which are pricked into the surface of the skin at sites located above such receptor regions. However, also other forms of electrodes than the ones illustrated are possible. The treatment current generator 2 is arranged in a small housing 5 to be carried on the body, which housing also accommodates the batteries required for feeding the treatment current generator. The treatment current generator 2 is provided with a microchip 17 capable of being programmed, which controls the course of the treatment current.

Housing 5 of the punctual stimulation therapy appliance 1 approximately has the geometric form of a calotte cut from an ellipsoid, and at the base 6 of the calotte it carries a surface electrode disk 7 projecting laterally beyond this base, which is designed to be adhesive at its side facing away from the calotte. The surface electrode disk 7 is provided as a base electrode for supplying the treatment current, which means that it closes the treatment current circuits leading from the treatment current generator 2 to the electrodes 4 and, from there, to the stimulating receptor regions, and back to the treatment current generator 2 with which this surface electrode disk 7 is electrically connected.

Preferably, the surface electrode disk 7 is a disk 8 made of an electrically insulating flexible material, which disk is seated with one of its surface sides 9 on the housing 5 of the appliance 1 and, on its other surface side 10 which faces away from the housing 5 of the appliance has an electrically conductive layer 11. In the case illustrated, this electrically conductive layer 11 of the surface electrode disk 7 is connected to the treatment current generator 2 by means of contact connectors 15 passing through the insulating material of disk 8. To intensify the electrical and mechanical contact between the side 10 comprising the electrically conductive layer 11 of the surface electrode disk 7 and the surface of the skin onto which this appliance is put so as to close the aforementioned electric circuits of the treatment currents leading over the receptor regions, preferably an electrically conductive gel not illustrated in detail in the drawings is provided.

When using the electric stimulation therapy receptor regions located of the external ear are stimulated. Both, with a view to guiding the lines 3 through which the treatment currents reach the electrodes 4 and with a view to the stimulating currents flowing over the receptor regions it is advantageous that the appliance provided with a surface electrode is arranged in the region of the ear on the surface of the skin. For this it is suitable if the surface electrode disk 7 has an indentation 13 on at least one location of its peripheral rim 12, whereby the appliance can be placed easily tightly behind the ear, which has advantages as regards the frequently desired discreetness and as regards a good fit and also as regards the electric stimulation. Besides, the surface electrode disk 7 projects substantially all around by the same width beyond the rim 14 of the base 6 of the calotte. By this protrusion of the surface electrode disk 7, this flexible disk can be pressed snugly to the surface of the skin at the site of application of the appliance without any problems, the adhesive design of the disk resulting in a good and secure hold although the skin surface often is not even. In this respect it is suitable that the surface side 9 of the disk facing the calotte is electrically insulating so that pressing manipulations acting on this disk with the appliance turned on will not have any immediate effect on the electrical conditions.

In the case illustrated, the housing 5 of appliance 1 has an inner housing part 16 accommodating the treatment current generator 2 provided with, the programmable microchip 17, furthermore feeding batteries 18, a printed board 19 forming the electric connections of the appliance, and treatment current exit contacts 20, and furthermore, an outer housing part 21 in the form of a calotte-type cap which can be snapped onto the inner housing part 16 so as to cover the latter. The surface electrode disk 7 is fixed on rim 22 of inner housing part 16, e.g. glued or welded thereto. Contact connectors 15 lead from the outer surface side 10 of the surface electrode disk 7 through the insulating material of disk 8 to the treatment current generator 2, thereby connecting this electrically conductive layer 11 to the treatment current generator 2. Connecting contacts 23 form electrical connections between the individual feeding batteries 18 and from these feeding batteries to the treatment current generator 2. In the exemplary embodiment illustrated, furthermore, a switch 41 is arranged in the inner housing part 16, which switch is incorporated in the current supply of the treatment current generator 2 and which, in the at-rest position, is in its "OFF" position and can be moved into the "ON" position by pressing thereon, a pin not illustrated either in detail for pressing thereon being provided on outer housing part 21, the switch being movable into the "ON" position by means of this pin when the outer housing part 21 is snapped onto the inner housing part 16. Advantageously, an interface connection is provided on or in the inner housing part 16 or on the printed board 19, via which interface connection the programmable microchip 17 which, as mentioned above, advantageously is in the form of a microcontroller or microprocessor, can be programmed according to the respective stimulation aim.

The invention claimed is:

1. A punctual stimulation therapy method comprising the following steps:
   placing a punctual stimulation therapy device having a housing adjacent to a patient's outer ear;
   providing a battery operated treatment current generator disposed in said housing and having a programmable microchip for controlling a treatment current course with respect to a desired waveform, amplitude and timing of a treatment current;
   providing a surface electrode disk coupled to a surface of said housing and to said treatment current generator, said electrode disk acting as a base electrode for supplying a treatment current to the patient in a region of said patient's outer ear; and
   providing at least one needle electrode which serves as a puncturing means for puncturing a patient's skin and for applying an electrical current to a patient and to hit a receptor region in a patient's external ear.

2. A punctual stimulation therapy appliance for use with a battery, the appliance comprising:
   a) a housing which is sized to be worn in a region adjacent to a region of an outer ear;
   b) a battery operated treatment current generator disposed in said housing;
   c) a surface electrode disk disposed on a surface of said housing and coupled to said treatment current generator, said electrode disk acting as a base electrode for supplying a treatment current to the patient in a region of a patient's outer ear;
   d) a plurality of needle electrodes each being physically separate from each other and each having a needle top and being coupled to said treatment current generator via an independent flexible line wherein each of said needle electrodes is connected to said treatment current generator;
   wherein said treatment current generator comprises at least one programmable microchip for controlling a treatment current course with respect to a desired waveform, amplitude and timing of a treatment current;
   wherein said housing is shaped approximately as a calotte cut from an ellipsoid, and, wherein the device further comprises a flexible surface electrode disk laterally projecting beyond the said housing and designed to be adhesive at its side facing away from said calotte shaped housing, wherein said surface electrode disk acts a base electrode for supplying the treatment current and is connected to the treatment current generator.

3. A punctual stimulation therapy appliance according to claim 2, wherein said programmable microchip may be programmed from the outside in each case for the digital synthesis of the respective desired waveform and amplitude of the treatment current.

4. A punctual stimulation therapy appliance according to claim 2, wherein said programmable microchip has a memory in which several waveforms and amplitudes of the treatment current are stored and can optionally be called.

5. A punctual stimulation therapy appliance according to claim 2, wherein said programmable microchip may be programmed for controlling the length of the current flow intervals and current flow pause intervals in the course of treatment sequences and/or the duration of rest pauses provided between the treatment sequences.

6. A punctual stimulation therapy appliance according to claim 2, wherein said programmable microchip has a memory in which in each case, said memory stores and optionally calls several values for the duration of current flow intervals and current flow pause intervals to be used in treatment sequences and/or for the duration of rest pauses to be provided between treatment sequences.

7. A punctual stimulation therapy appliance according to claim 2, wherein said programmable microchip is a microprocessor, or microcontroller, respectively.

8. A punctual stimulation therapy appliance according to claim 2, wherein said surface electrode disk is a disk formed of electrically insulating flexible material which with its one surface side is seated on the housing of the appliance and at its other surface side which faces away from the housing of the appliance has an electrically conductive layer.

9. A punctual stimulation therapy appliance according to claim 8, wherein said electrically conductive layer of the surface electrode disk is connected to the treatment current generator by contact connectors passing through the insulating material of the disk.

10. A punctual stimulation therapy appliance according to claim 2, further comprising an electrically conductive gel that is provided for intensifying the electrical and mechanical contact between the side of the surface electrode disk provided with the electrically conductive layer and the surface of the skin.

11. A punctual stimulation therapy appliance according to claim 2, wherein said surface electrode disk has an indentation and otherwise projects substantially all around with an equal width beyond the rim of the base of the calotte.

12. A punctual stimulation therapy appliance according to claim 2, wherein said housing has an inner housing part accommodating said treatment current generator having said programmable microchip, a plurality of feeding batteries, a printed board forming electrical connections, and treatment current output contacts, and an outer housing part having the shape of a calotte-type cap capable of being snapped on an inner housing part so as to cover the latter, wherein said surface electrode disk is fixed at the rim of said inner housing part.

13. A punctual stimulation therapy appliance according to claim 12, further comprising a switch that is arranged in said inner housing part, wherein said switch is included in the current supply of the treatment current generator and which, in the at-rest position, is in its "OFF" position and can be moved into its "ON" position by pressing thereon, a pin for pressing thereon being provided on outer housing part, the switch being movable into its "ON" position by means of this pin when the outer housing part is snapped onto the inner housing part.

* * * * *